(12) United States Patent
Moore

(10) Patent No.: US 12,109,142 B1
(45) Date of Patent: Oct. 8, 2024

(54) MEDICAL DEVICE FOR PLACING ON A HUMAN PENIS

(71) Applicant: The PhalloFill Clinics, LLC, Dallas, TX (US)

(72) Inventor: William Allen Moore, Dallas, TX (US)

(73) Assignee: The PhalloFill Clinics, LLC, Dallas, TX (US)

( * ) Notice: Subject to any disclaimer, the term of this patent is extended or adjusted under 35 U.S.C. 154(b) by 0 days.

(21) Appl. No.: 18/367,629

(22) Filed: Sep. 13, 2023

(51) Int. Cl.
*A61F 5/41* (2006.01)
*A61F 2/26* (2006.01)

(52) U.S. Cl.
CPC .................. *A61F 5/41* (2013.01); *A61F 2/26* (2013.01); *A61F 2005/414* (2013.01); *A61F 2250/0097* (2013.01)

(58) Field of Classification Search
CPC . A61F 5/41; A61F 2005/411; A61F 2005/414
See application file for complete search history.

(56) References Cited

U.S. PATENT DOCUMENTS

| | | | | |
|---|---|---|---|---|
| 844,798 A | * | 2/1907 | Hawley | A61F 5/41 128/845 |
| 3,131,691 A | * | 5/1964 | Scott | A61F 5/41 600/39 |
| 3,401,687 A | * | 9/1968 | Hood | A61F 5/41 600/39 |
| 4,869,241 A | * | 9/1989 | Friedmann | A61F 5/41 128/842 |
| 4,995,381 A | * | 2/1991 | Marmar | A61F 5/41 600/39 |
| 5,360,390 A | * | 11/1994 | Maanum | A61F 5/41 600/39 |
| 5,535,758 A | * | 7/1996 | Hagihara | A61F 5/41 600/38 |
| 5,779,621 A | * | 7/1998 | Chaney | A61F 5/41 600/38 |
| 6,015,379 A | * | 1/2000 | Sachse | A61F 5/41 600/38 |
| 6,390,095 B1 | * | 5/2002 | Magnusson | A61F 5/41 128/842 |
| 9,622,902 B1 | * | 4/2017 | Bublick | A61F 6/04 |
| 2005/0085788 A1 | * | 4/2005 | Tomosada | A61F 5/41 604/500 |
| 2008/0076964 A1 | * | 3/2008 | Jared | A61F 5/41 600/39 |
| 2009/0113605 A1 | | 5/2009 | Nicolosi et al. | |
| 2010/0179379 A1 | * | 7/2010 | Park | A61F 5/41 600/41 |

(Continued)

*Primary Examiner* — Carrie R Dorna
(74) *Attorney, Agent, or Firm* — Nixon & Vanderhye P.C.

(57) ABSTRACT

A medical device for placing on a human penis, e.g., post penile enhancement procedure, includes a flexible sleeve having a proximal end and a distal end, the proximal end being sized and dimensioned to be positioned over the base of the penis, the sleeve being configured and sized to extend from the base of the penis and along the body of the penis, the distal end being sized and dimensioned to terminate just below the corona of the glans of the penis. The distal end may include a flange that extends radially outwards from an outer surface of the sleeve, and a thickness of the sleeve spaced away from the flange along a longitudinal axis of the sleeve may be about 4 mm-5 mm.

24 Claims, 17 Drawing Sheets

(56) References Cited

U.S. PATENT DOCUMENTS

| | | |
|---|---|---|
| 2012/0016189 A1 | 1/2012 | Gioia |
| 2014/0073851 A1 | 3/2014 | Gioia |
| 2017/0135895 A1 | 5/2017 | Jafri |
| 2019/0060103 A1 | 2/2019 | Fielding |
| 2020/0360172 A1 | 11/2020 | Smith et al. |
| 2022/0331142 A1 | 10/2022 | Paz |
| 2023/0103972 A1 | 4/2023 | Loria |

* cited by examiner

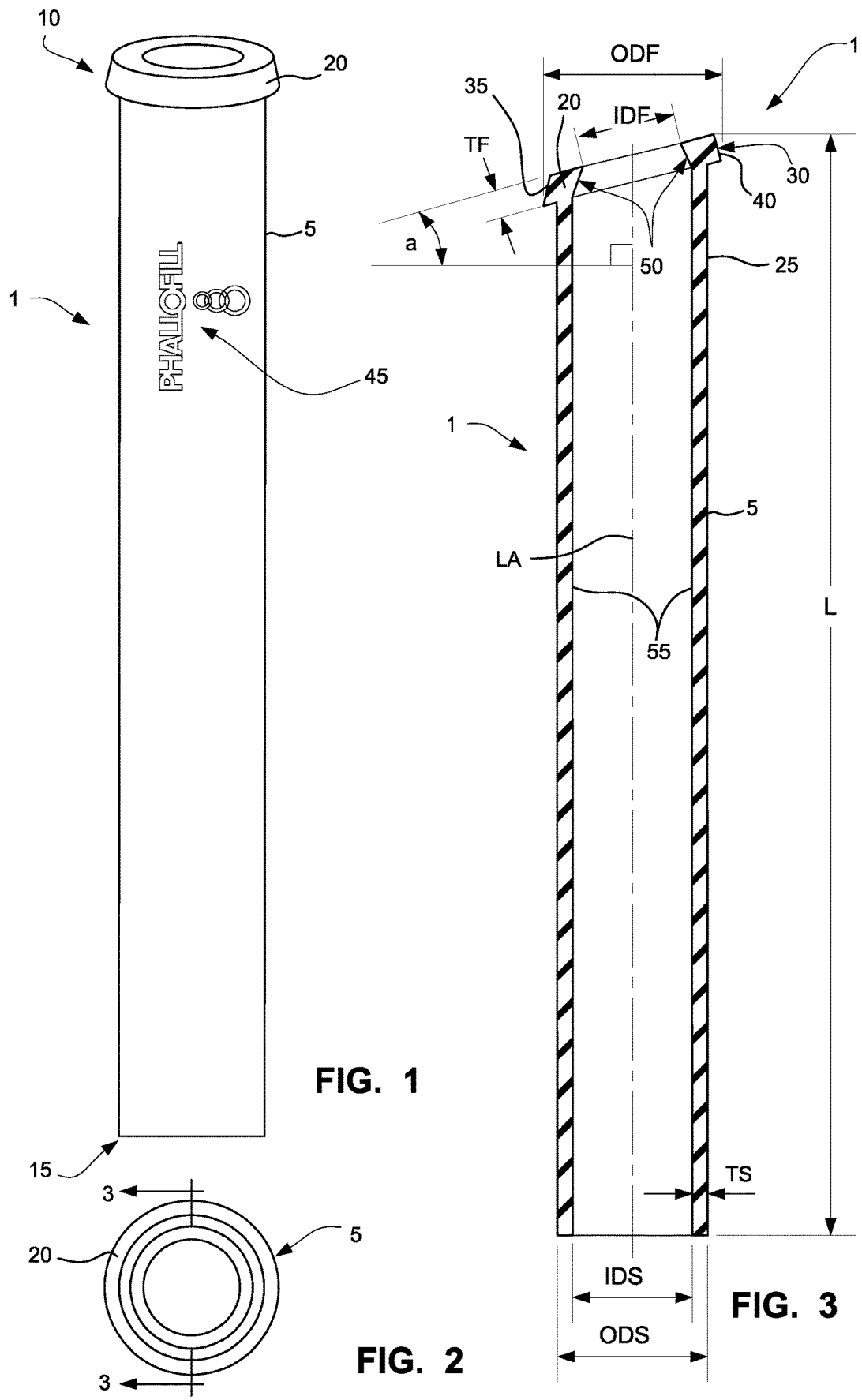

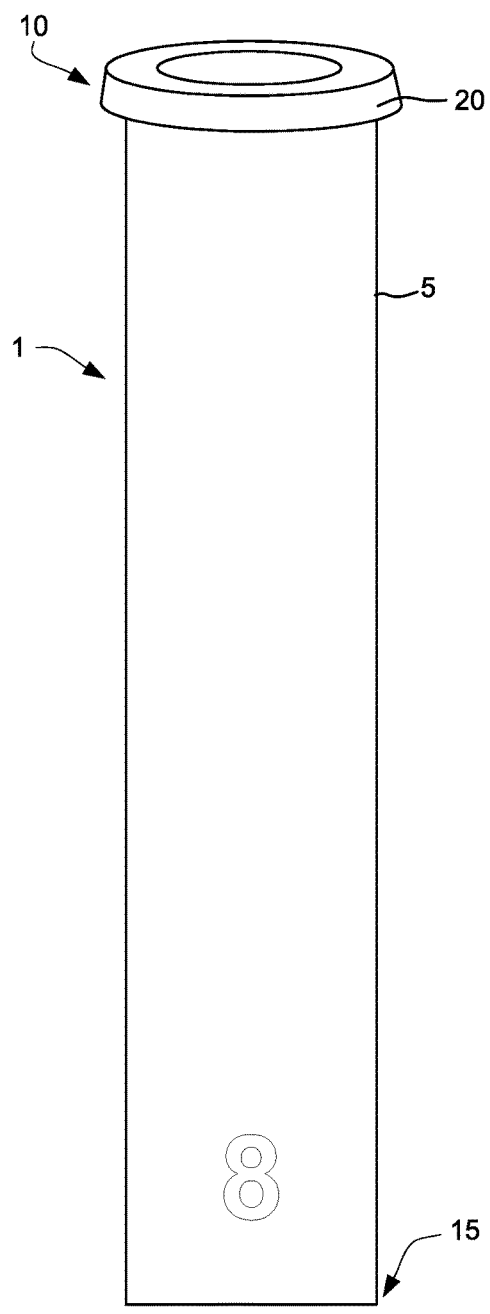
FIG. 12A
FIG. 12B
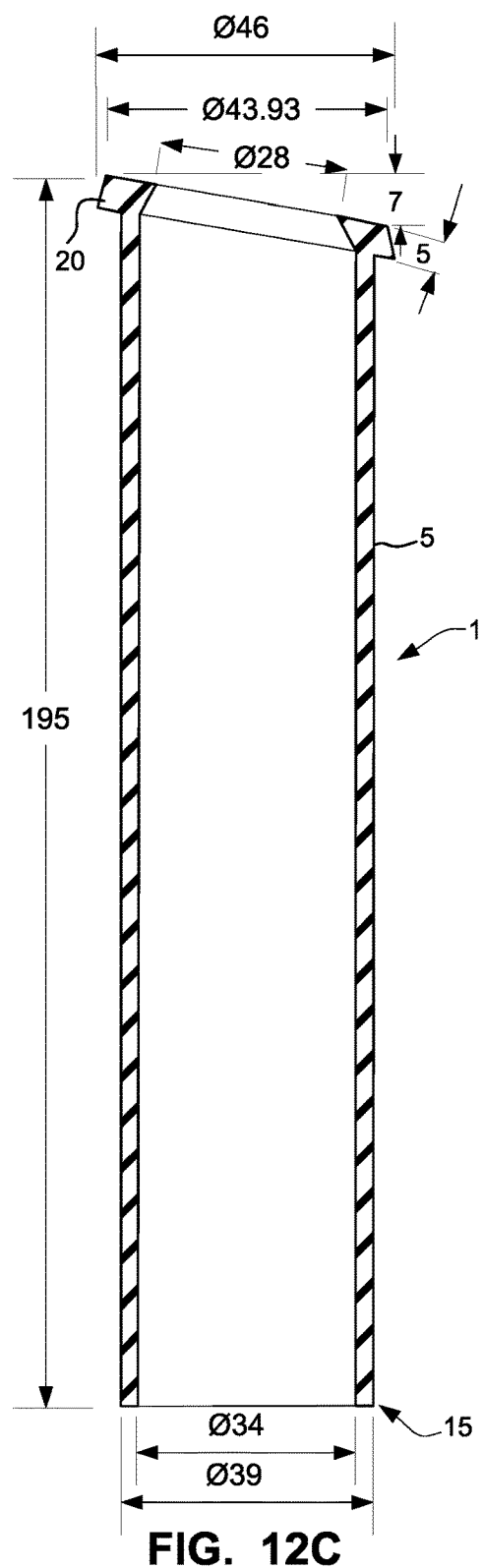
FIG. 12C

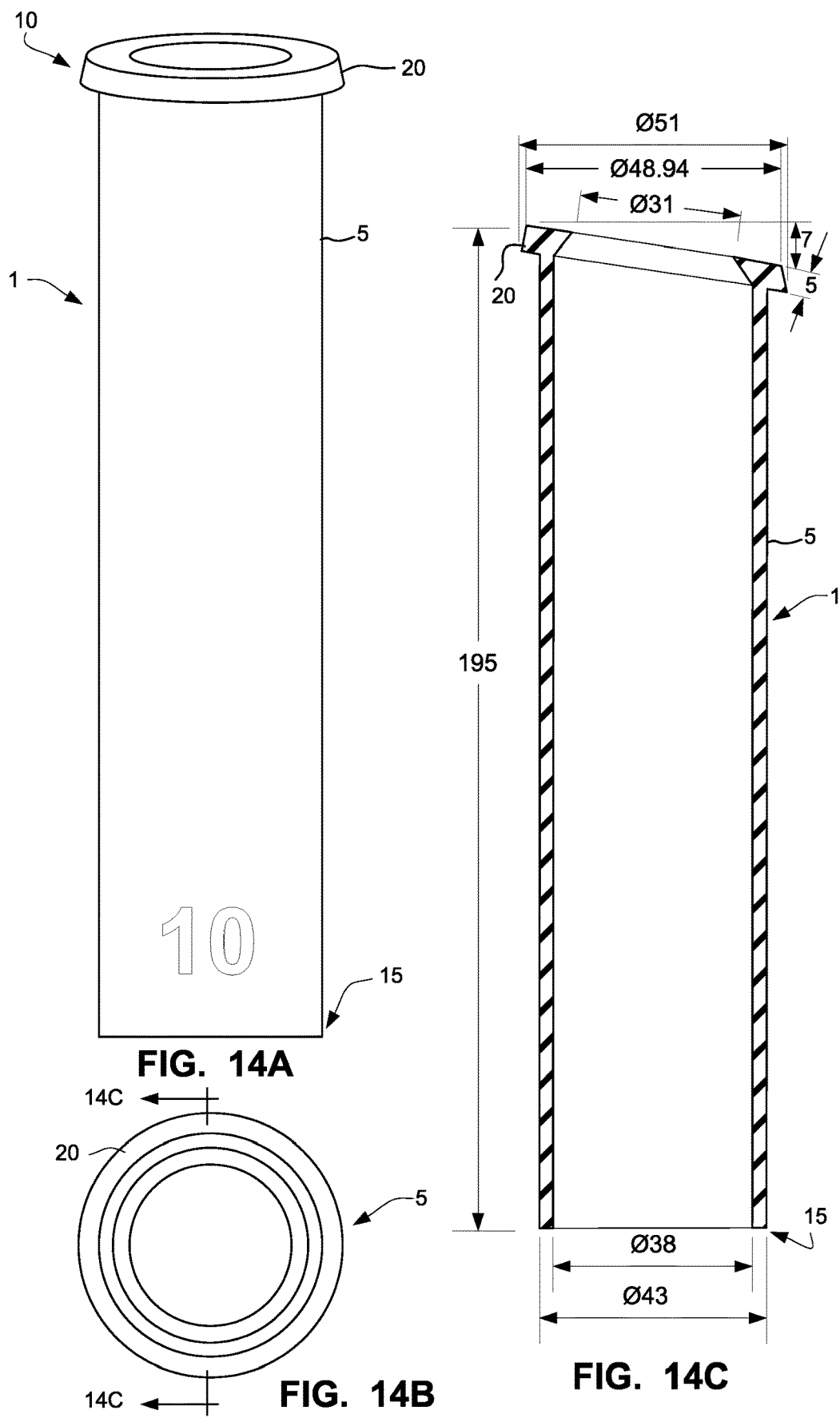

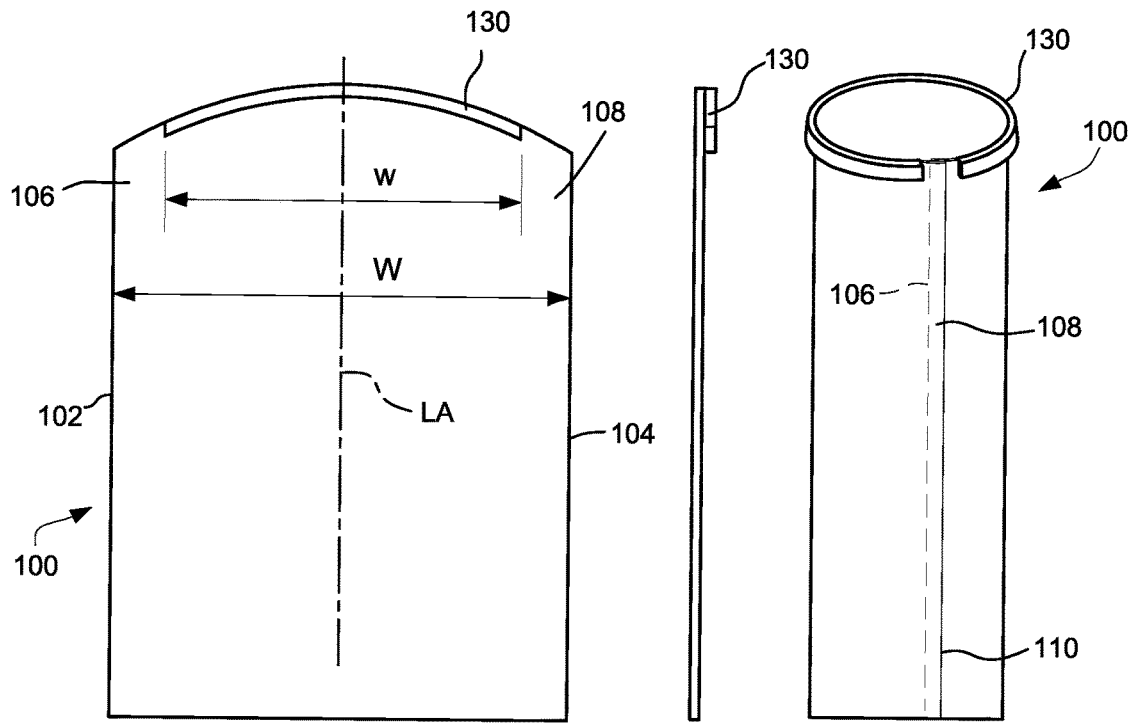
FIG. 15  FIG. 16  FIG. 18
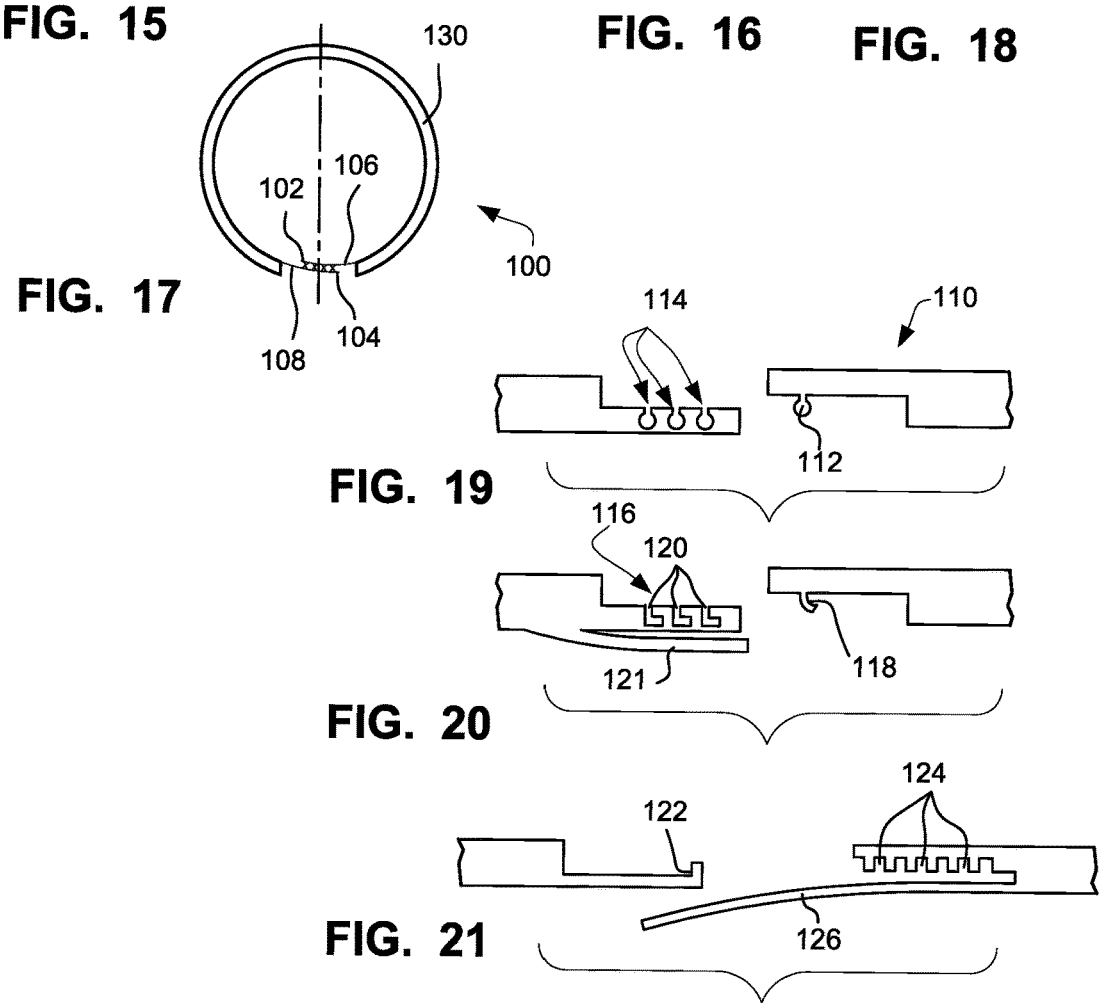
FIG. 17
FIG. 19
FIG. 20
FIG. 21

MEDICAL DEVICE FOR PLACING ON A HUMAN PENIS

CROSS-REFERENCE TO RELATED APPLICATIONS

NONE.

BACKGROUND & SUMMARY

Penile shaft girth enhancement is a procedure that can address aesthetic or genetic concerns. Such enhancement can be performed surgically or non-surgically. Following procedure and/or surgery, the penis is commonly wrapped with an ace bandage.

One aspect of the present technology is to provide a medical device, e.g., a sleeve, that can improve upon current treatment following a penile procedure/surgery.

The present technology relates generally to a medical device, e.g., a sleeve, for placing on a human penis, e.g., following penile enhancement procedure and/or surgery.

One aspect of the present technology is directed to a medical grade silicone sleeve or sheath structured to, for example, compress and/or elongate a penis from the base (proximal shaft) to just below the corona of the glans (head of the penis).

Another aspect of the present technology is to provide a medical device for placing on a human penis, the medical device comprising: a flexible sleeve having a proximal end and a distal end, the proximal end being sized and dimensioned to be positioned over the base of the penis, the sleeve being configured and sized to extend from the base of the penis and along the body of the penis, the distal end being sized and dimensioned to terminate just below the corona of the glans of the penis.

The distal end may include a flange that extends radially outwards from an outer surface of the sleeve, wherein the flange is about 5 mm in thickness, and wherein a thickness of the sleeve spaced away from the flange along a longitudinal axis of the sleeve is about 2 mm-3 mm, or 2.5 mm.

The thickness of the sleeve may be about 1-4 mm, e.g., 2.5 mm from the distal end to the proximal end.

The sleeve may have a wall thickness of about 0.5 to about 10 mm, e.g., about 1 mm to about 5 mm, about 2-4 mm, or 2 mm, 2.5 mm or 3 mm.

The sleeve may have an inner diameter of about 15-60 mm, or about 20-40 mm.

The sleeve may come in a variety of sizes, having an inner diameter of about 20 mm, 22 mm, 24 mm, 26 mm 28 mm, 30 mm, 32 mm, 34 mm, 36 mm or 38 mm. Larger diameters are contemplated as well, including 40 mm, 42 mm 44 mm or 46 mm.

In examples, the length of the sleeve is about 180-220 mm, or about 195 mm (which may be cut to size).

In examples, the sleeve is configured to be moved from an unrolled positioned to a rolled position by rolling the proximal end radially outwards and axially towards the distal end. In the rolled position, the sleeve is stretchable from a first diameter to a second diameter.

In examples, the sleeve is in the form of a substantially flat sheet with longitudinal edges or margins that are joined to one another at a seam In examples, the sleeve includes an indicator or indicia (e.g., a logo and/or arrow) to indicate what side is intended to be the superior side when in place on the penis.

In examples, the distal end includes a flange that extends radially outwards from an outer surface of the sleeve.

In examples, an inner diameter of the flange is less than an inner diameter of the distal end of the sleeve.

In examples, the flange is contained in a plane that is angled relative to a longitudinal axis of the sleeve. If no flange is provided, the sleeve can be cut or made at such an angle. The angle allows the sleeve to match a shape of the corona of the glans of the penis. The flange angle may be about 1-15 degrees, or about 4-6 degrees.

In examples, a diameter of the flange is about 2-10 mm (e.g., 4-5 mm) greater than an outer diameter of the sleeve spaced axially away from the flange.

In examples, a thickness of the flange if about 2-8 mm, e.g., about 5 mm.

In examples, the flange has a circumferential wall that defines a variable wall angle with respect to a longitudinal axis of the sleeve. For example, the wall angle varies around the circumference of the wall, with a superior portion of the wall having a superior wall angle that is different than an inferior portion of the wall.

In examples, an inner diameter of the flange includes an inwardly angled portion (e.g., in the form of a cone shape) that forms an angle relative to an inner surface of the sleeve adjacent the flange.

In examples, the sleeve is made of medical grade, biocompatible silicone, a textile and/or a thermoplastic elastomer.

In examples, the sleeve has a closed loop shape in cross section, e.g., circular, oval, or nearly oval or circular, and may have a solid wall portion from the distal end to the proximal end with no openings or interruptions. The circumference of the sleeve may be constant from the proximal end to the distal end, but the circumference could taper down (e.g., 1-2 mm) from the proximal end to the distal end.

In examples, the sleeve is configured to compress and/or elongate the penis.

In examples, the sleeve is configured to resist migration of at least one girth enhancement product injected into the penis.

In examples, the at least one girth enhancement product includes a dermal filler, fat graft, or girth enhancement device.

Another aspect of the present technology is directed to a kit for post procedural treatment for penile enhancement, including a plurality of flexible sleeves, wherein each said sleeve has a different inner diameter but substantially the same length and the substantially same thickness.

In examples, the plurality of flexible sleeves includes 2-15 said sleeves, e.g., 10 sleeves, and the plurality of sleeves may include 4-6 said sleeves.

Another aspect of the present technology is to provide a medical grade silicone sleeve or sheath structured to compress and/or elongate a penis from the base or proximal shaft of the penis to just below the corona of the glans or head of the penis.

This disclosure will now provide a more detailed and specific description that will refer to the accompanying drawings. The drawings and specific descriptions of the drawings, as well as any specific or alternative examples discussed, are intended to be read in conjunction with the entirety of this disclosure. The medical device may, however, be embodied in many different forms and should not be construed as being limited to the examples set forth herein; rather, these examples are provided by way of illustration only and so that this disclosure will be thorough, complete, and fully convey understanding to those skilled in the art. Moreover, one or more features of one example may be used in conjunction with any and all of the alternate examples.

BRIEF DESCRIPTION OF THE DRAWINGS

FIG. 1 is a front view of a medical device according to an example of the present technology.

FIG. 2 is a bottom view taken from the proximal end of the medical device shown in FIG. 1

FIG. 3 is a cross-sectional view taken along line 3-3 of FIG. 2.

FIGS. 12A-12C illustrate views of an eighth size of a medical device according to an example of the present technology.

FIGS. 14A-14C illustrate views of a tenth size of a medical device according to an example of the present technology.

FIGS. 15-18 show a variation of a medical device or sleeve according to the present technology.

FIGS. 19-21 illustrate examples of how marginal edges (or flanges) of the sleeve shown in FIGS. 15-18 can be releasably connected.

DETAILED DESCRIPTION OF EXAMPLE NON-LIMITING EXAMPLES

Figure 4A:
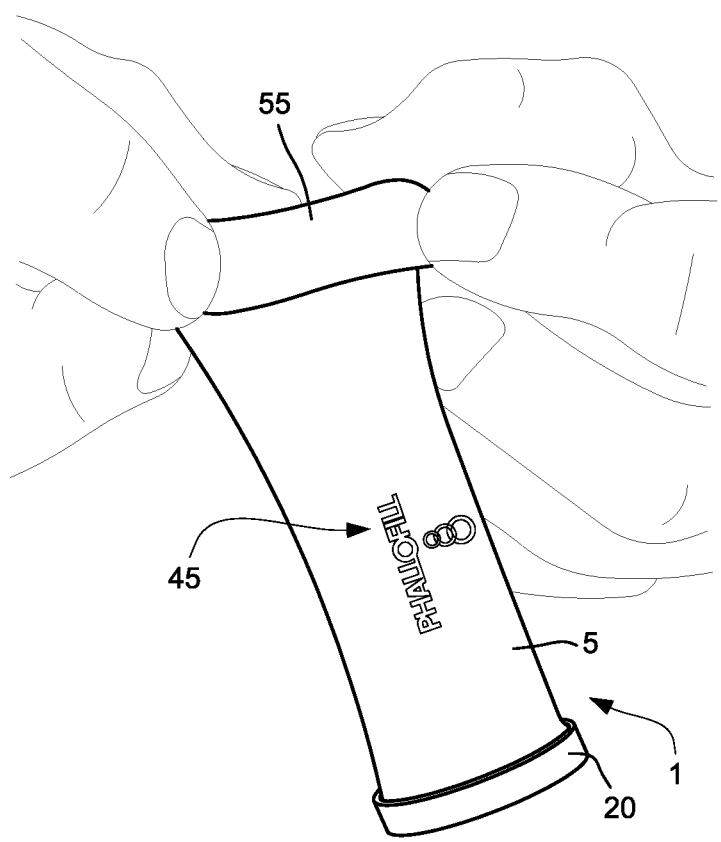
FIGS. 4A-4F illustrate an example of how the medical device of the present technology is applied to a model human subject.
Figure 4B:
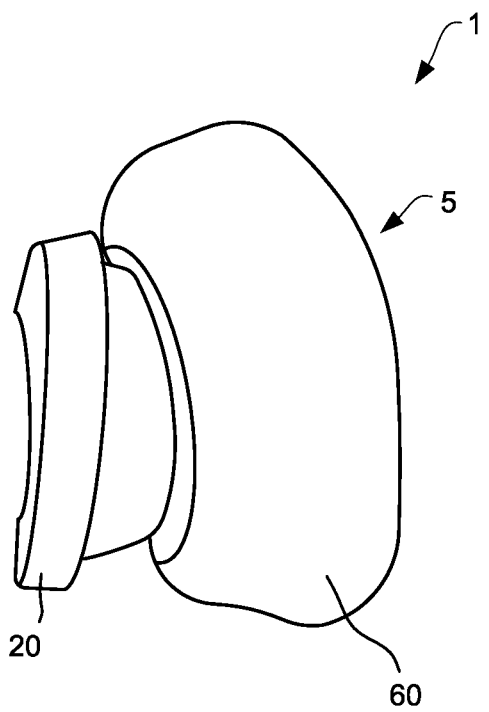

The present technology is directed to medical device configured to be worn by a human. In an example, the medical device is in the form of a sleeve or a sheath configured to cover a portion of a human penis, e.g., following a procedure, e.g., a surgical procedure. However, the sleeve or sheath can also provide benefits to a user even if the user has not been subject to a procedure or surgery. For example, the sleeve can provide some lengthening on its own and/or prevent some retraction even if the user has not been subject to a procedure or a surgery.

FIG. 1 illustrates a front view of a medical device 1, which may take the form of a sleeve 5 (or sheath). The sleeve 5 may include a distal end 10 and a proximal end 15. The proximal end 15 is sized and configured to be positioned over the base of the penis. The sleeve 5 is configured and sized to extend from the base of the penis and along the body of the penis. The distal end 10 is sized and configured to terminate just below the corona of the glans of the penis, as seen, for example, in FIGS. 4E-4F.

The sleeve may have a closed loop shape in cross section, as seen in FIGS. 2 and 3. The sleeve 5 may have a solid wall portion from the distal end to the proximal end, e.g., with substantially no openings or interruptions.

The distal end may include a flange 20 that extends radially outwards from an outer surface 25 of the sleeve 5.

Dimensions and/or Geometry

The thickness TS of the sleeve 5 is about 0.5 mm to about 10 mm from the distal end to the proximal end, not including the flange 20. In examples the thickness is about 1 mm to about 4 mm. The thickness may be about 2-3 mm, or 2.5 mm. The thickness TS could vary based on the diameter of the sleeve 5, or the thickness can remain constant regardless of the diameter (e.g., inner diameter IDS) of the sleeve, as described in relation to the kit of sleeves below. This thickness (e.g., 2.5 mm) or range of thicknesses has been found to be beneficial, e.g., in terms of allowing the sleeve to be manipulated and/or providing medical benefits to the user, as described herein. For example, this thickness allows for the sleeve to be rolled and stretched during placement on the penis, and also allows nocturnal erections (expansion) yet is still firm or rigid enough to hold the penis extended without having folds or "wrinkles" in the sleeve. The sleeve may be relatively more rigid in the axial direction, and relatively more flexible in the circumferential direction. Sleeves with thicknesses outside this range (e.g., below 2 mm or above 4 mm) can still be used, but may not work as well. In addition, the thickness TS of the sleeve 5 could vary along the longitudinal axis LA, e.g., the thickness at the proximal end could be more than the thickness at the distal end, and gently tapered therebetween.

The inner diameter IDS of the sleeve is about 15-50 mm, or it may be about 20-40 mm. The inner diameter IDS may be 20 mm, 22 mm, 24 mm, 26 mm 28 mm, 30 mm, 32 mm, 34 mm, 36 mm or 38 mm. Larger sizes are available as well, including 40 mm, 42 mm, 44 mm, 46 mm, etc.

A length L of the sleeve is about 180-220 mm, e.g., about 195 mm.

The flange 20 is contained in a plane P that is angled at a flange angle a relative to a longitudinal axis LA of the sleeve 5. The flange angle a is about 1-15 degrees, or about 3-6 degrees. The angle is selected to match the shape of the corona of the glans of the penis. If no flange is provided, the distal end of the sleeve is preferably angled to so match.

An outer diameter ODF of the flange 20 is about 2-10 mm, e.g., 4-5 mm, greater than the outer diameter ODS of the sleeve, spaced axially away from the flange 20. In an example, an inner diameter IDF of the flange 20 is less than an inner diameter IDS of the distal end 10 of the sleeve 20. Making the inner diameter less than the sleeve diameter should help to prevent the head of the penis from retracting into the sleeve.

In an example, a thickness TF of the flange 20 is about 2-8 mm, e.g., about 5 mm.

The flange 20 has a circumferential wall 30 that defines a variable wall angle with respect to the longitudinal axis LA of the sleeve. The wall angle varies around the circumference of the wall 30, e.g., with a superior portion 35 of the wall having a superior wall angle that is different than an inferior portion 40 of the wall.

In this context, the superior portion of the sleeve may be marked with an indicator or indicia 45, e.g., a logo and/or an arrow, to help the user or physician mount the sleeve 5 in the correct position on the user's penis. For example, the indicia 45 is positioned about a superior (top) surface of the penis that faces upwards when the user is in a standing position. The indicia 45 helps to align the flange 20 in the correct position relative to the corona of the glans of the penis. In another example, the indicia may be a line on the inner surface of the sleeve that is revealed when the sleeve is rolled. In another example, the top surface of the flange may include an alignment mark or arrow, as the flange is always visible even if the sleeve is rolled.

The inner diameter IDF of the flange 20 includes an inwardly angled portion 50 that forms an angle relative to an inner surface 55 of the sleeve adjacent the flange. In an example, the angled portion 50 forms a part of a cone, e.g., a truncated cone having a base diameter that is greater than the top diameter. In an example, the cone is asymmetric. The cone shape helps to prevent the penis from retracting into the sleeve.

Fitting the Sleeve

In an example, the sleeve 5 is configured to be moved from an unrolled position (e.g., FIGS. 1-3) to an at least partly rolled position (FIGS. 4A-4E) by rolling the proximal end 15 radially outwards and axially towards the distal end 10.

In the position shown in FIG. 4A, the user or physician begins to roll the proximal end 15, e.g., by turning the sleeve 5 inside-out, such that the inner surface 55 is exposed and rolled over the outer surface 25 It should be noted that prior to commencing the rolling operation, the user or physician may choose to cut the sleeve 5 to a length that is suitable for the given user or patient.

Figure 4C:
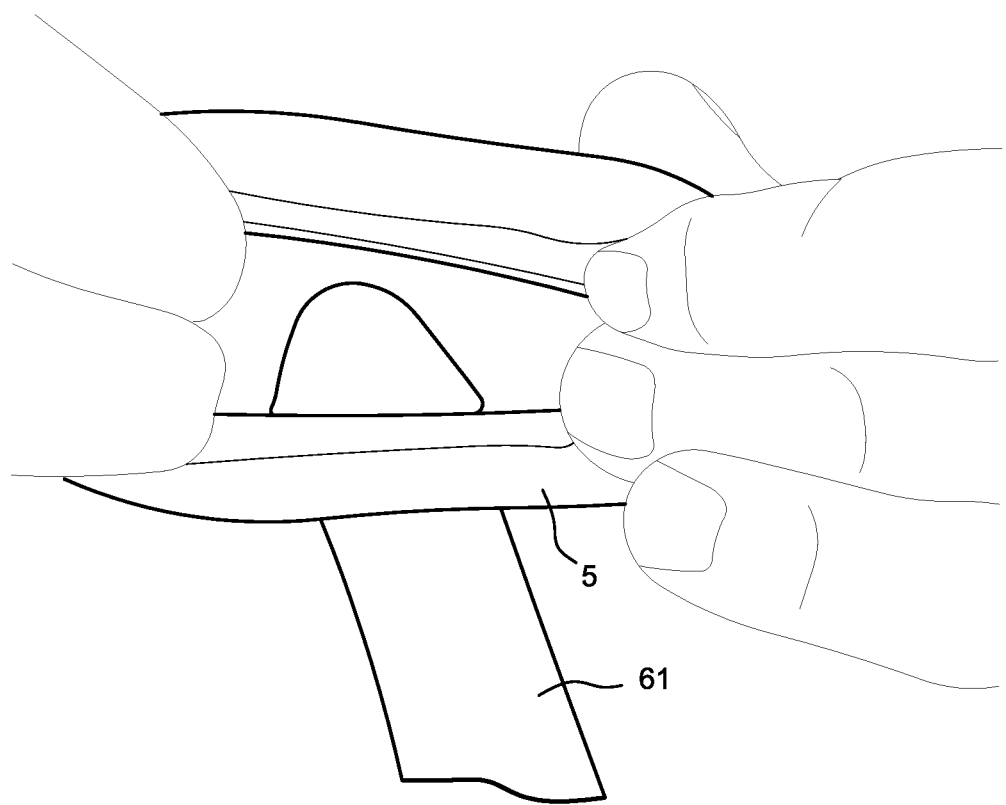

The user or physician continues to roll the sleeve 5 until the rolled part 60 is adjacent to or abuts the flange 20. In the rolled position of FIG. 4B, the sleeve 5 is stretchable from a first diameter (FIG. 4B) to a second diameter (FIG. 4C). For example, the sleeve should be stretchable to a diameter that is from 10-200% (e.g., 25-50%) of the rolled diameter in FIG. 4B. This helps avoid discomfort when passing the penis through the hollow sleeve 5.

Figure 4D:
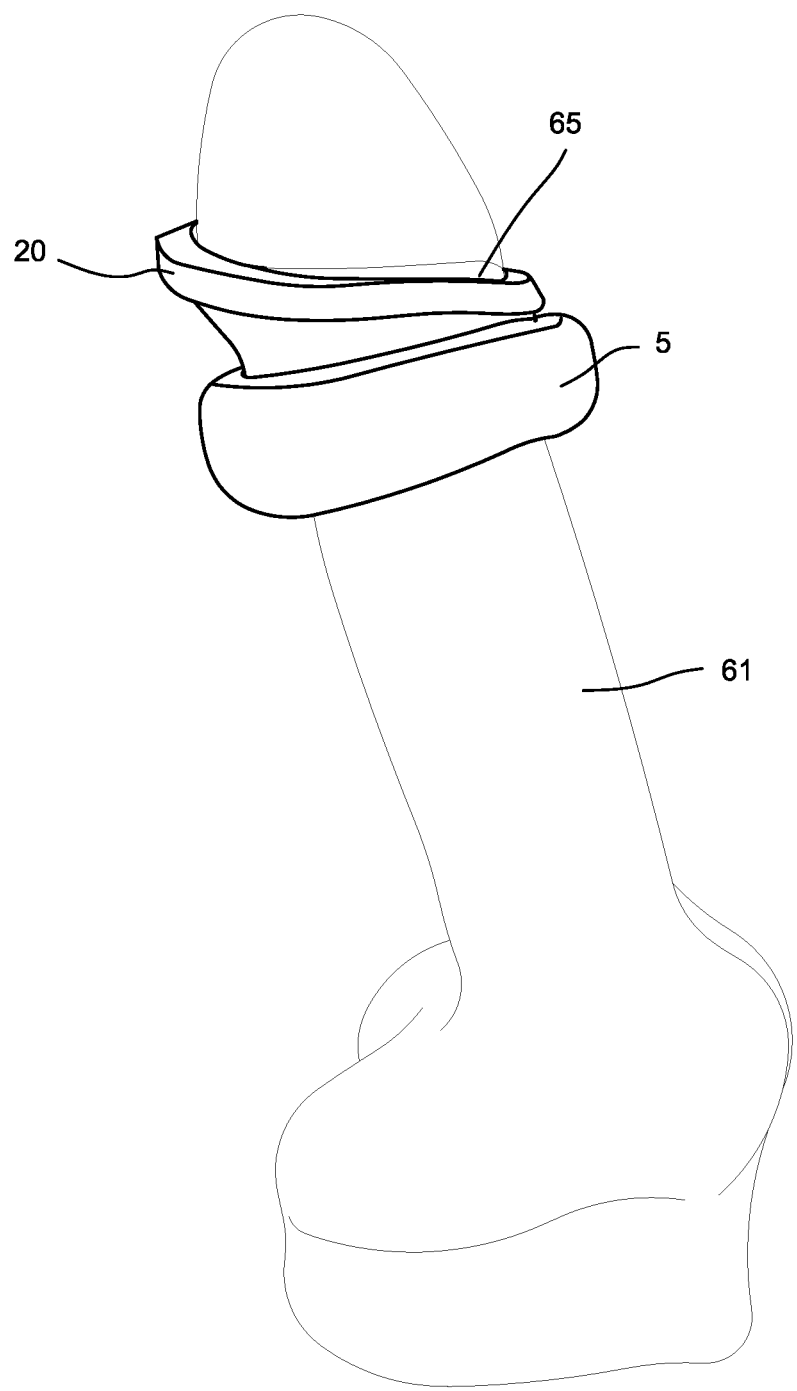

In FIG. 4D, the sleeve in its rolled up position is shown as being fit over a model penis 61, with the logo or indicia 45 positioned on the superior side of the penis. Thus the angle of the flange 20 substantially matches the angle of the corona 65 of the glans of the penis.

Figure 4E:
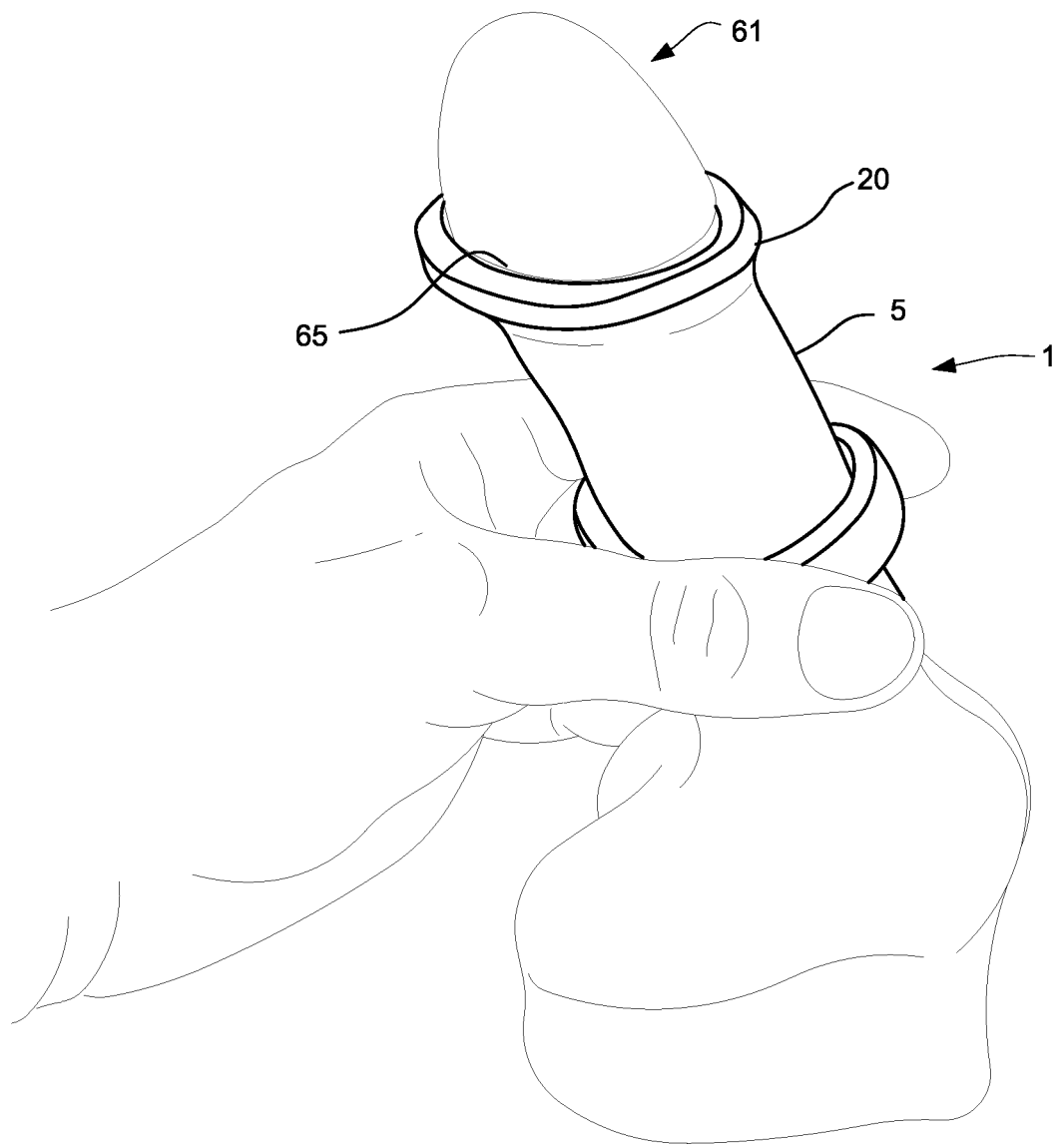
Figure 4F:
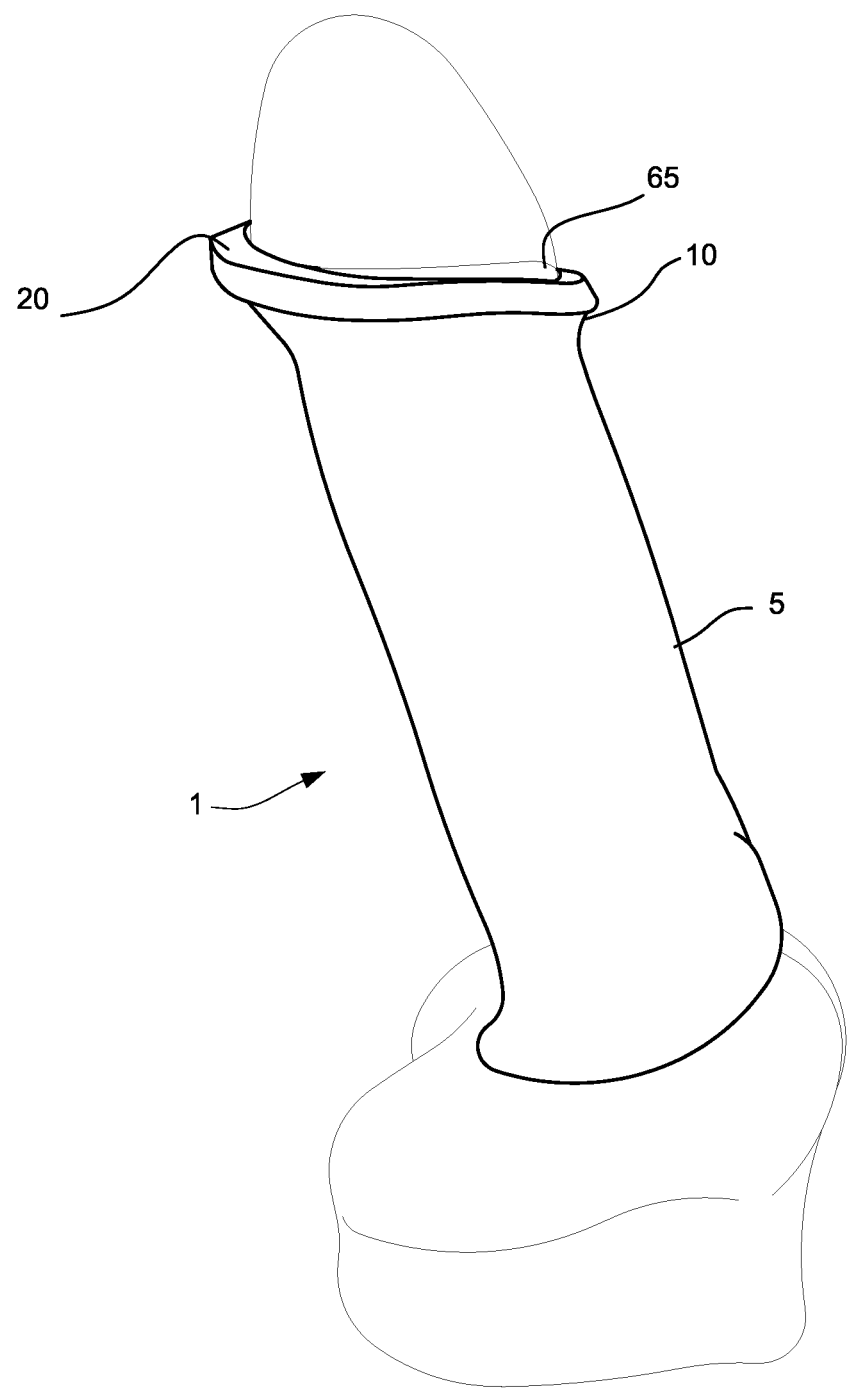
Figure 5A:
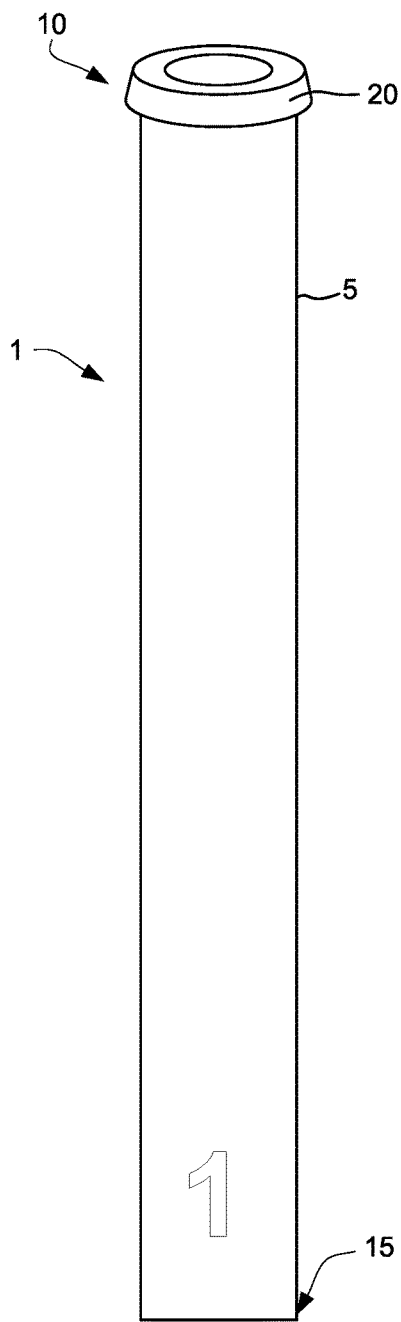
FIGS. 5A-5C illustrate views of a first size of a medical device according to an example of the present technology.
Figure 5B:
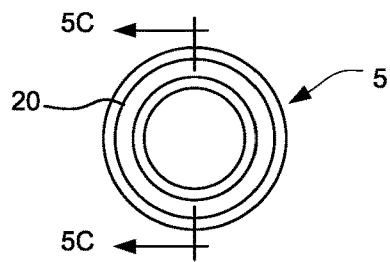
Figure 5C:
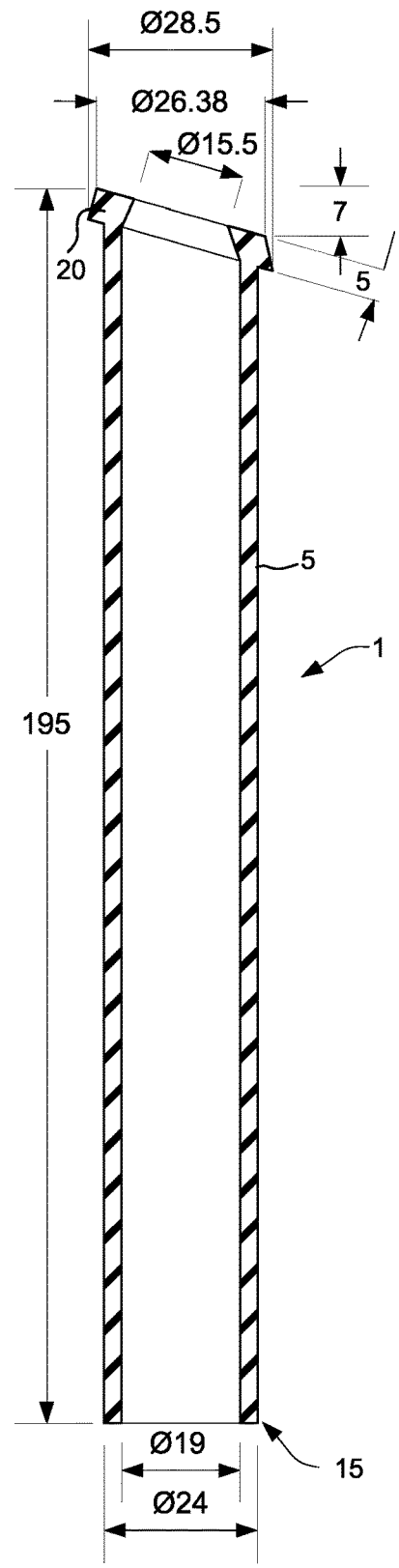

In FIG. 4E, the user or the physician (or clinician) rolls the sleeve 5 down towards the pubic bone or area of the user, and FIG. 4F shows the sleeve 5 in a completely unrolled state.

In the position shown in FIG. 4F, the sleeve 5 is configured to compress and/or elongate the penis, as the sleeve has a resiliency that tends to return the sleeve to its relaxed position (FIG. 1). The sleeve does not return to its fully relaxed position when in use, but instead is in a stretched position when in the "in use" position shown in FIG. 4F, e.g., 3-20%, e.g., 5-10%, to have the intended effect. Such circumferential compression of the shaft of the penis (when the sleeve wall is in tension due to stretch) also may help to keep the head of the penis from retracting into the sleeve.

To remove the sleeve, it may be cut along the axis with medically safe scissors, or the sleeve can be rolled back up (either direction, but preferably from the proximal end towards the distal end) whilst on the penis, and then stretched to overcome the head of the penis.

The sleeve is configured to resist migration of at least one girth enhancement product injected into the penis. The at least one girth enhancement product may include a dermal filler, fat graft, or girth enhancement device.

Materials

In an example, the sleeve is made of a rubber or elastic material, e.g., medical grade silicone or a thermoplastic elastomer. Table 1 below provides exemplary properties of the sleeve, e.g., the medical grade silicone, including hardness, density, resilience, tensile strength, tear strength, elongation and permanent set. The standard value represents a suitable range, which may vary from 5 to 20%, e.g., 8-12%. Test Standard, Unit and Test Value are also identified for each Testing Item in Table 1.

TABLE 1

| Testing Items | Test Standard | Unit | Standard Value | Test Value |
| --- | --- | --- | --- | --- |
| Hardness | GB/T 531.1-2008 | Shore A | 2-5 | 3 |
| Density | GB/T 533-2008 | g/m$^3$ | 1.07 ± 0.02 | 1.06 |
| Resilience | GB/T 1681-2009 | % | 25-35 | 25 |
| Tensile Strength | GB/T 528-2009 | MPa | 1-4 | 1.1 |
| Tear Strength | GB/T 529-2008 | kN/m | 5-20 | 6.8 |
| Elongation | GB/T 528-2009 | % | 700-900 | 853 |
| Permanent Set | GB/T 528-2009 | % | 1.7-4.3 | 4.3 |

The material, one or more of the properties shown in Table 1, geometry and/or one or more of the dimensions of the sleeve as described herein at least partly allow the sleeve to operate as described and/or provide the beneficial effects described herein.

The sleeve may be transparent or opaque. The sleeve may be customizable and include the patient's monogram or other customized features, such as a specific design or wording. The sleeve may come in a variety of colors, e.g., to match the skin of the patient.

The sleeve may be made of an elastic material, as described above. However, the sleeve may also be made of a textile material and/or an elastic material, e.g., a composite material having both textile and elastic materials. Textile materials can be made of resilient, stretchy material to allow the sleeve to apply compression to the penis when worn. Textile materials may be breathable, which might be beneficial to healing and comfort. Similarly, an elastic sleeve could be provided with perforations to allow for breathability.

Moreover, the sleeve may be manufactured to stretch in the circumferential direction, yet be relatively less stretchy in the axial direction. This can be accomplished by using rigidizers or textile threads that extend in the longitudinal direction, but not in the circumferential direction. In the circumferential direction, elastic threads may be provided to provide for the desired degree of stretch.

Kit

Figure 6A:
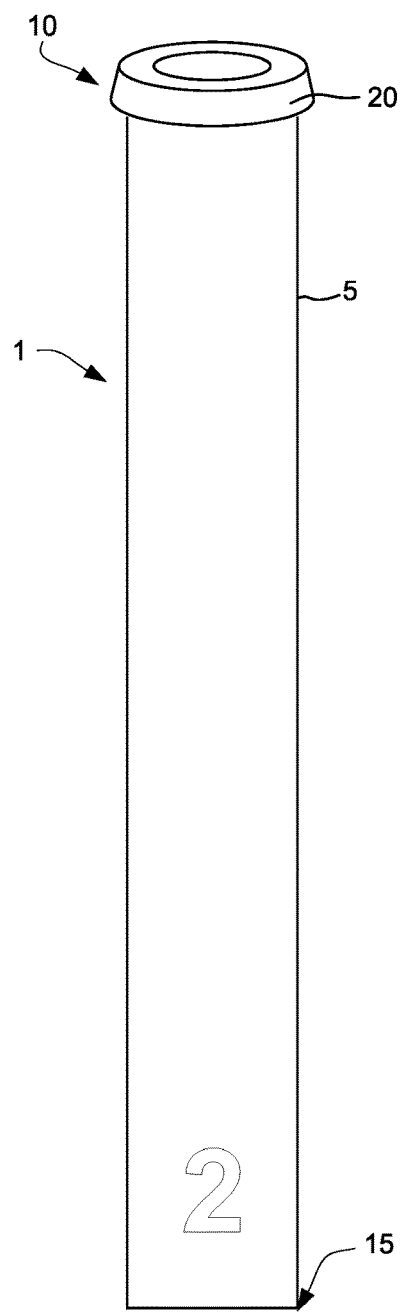
FIGS. 6A-6C illustrate views of a second size of a medical device according to an example of the present technology.
Figure 6B:
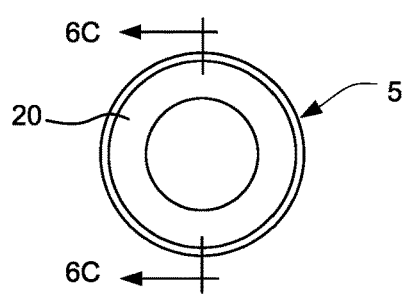
Figure 6C:
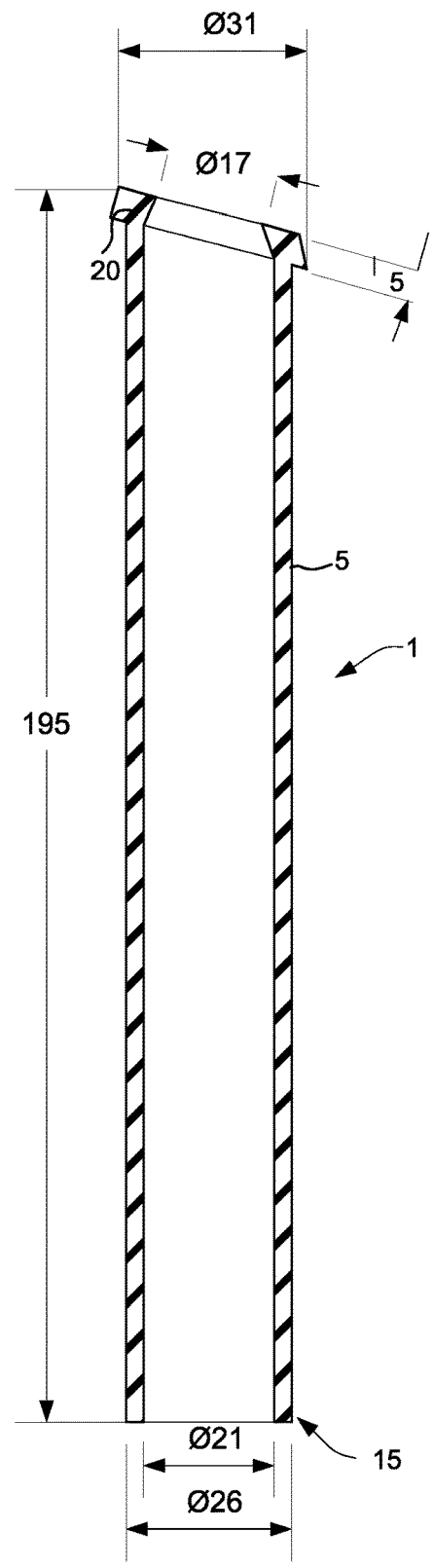
Figure 7A:
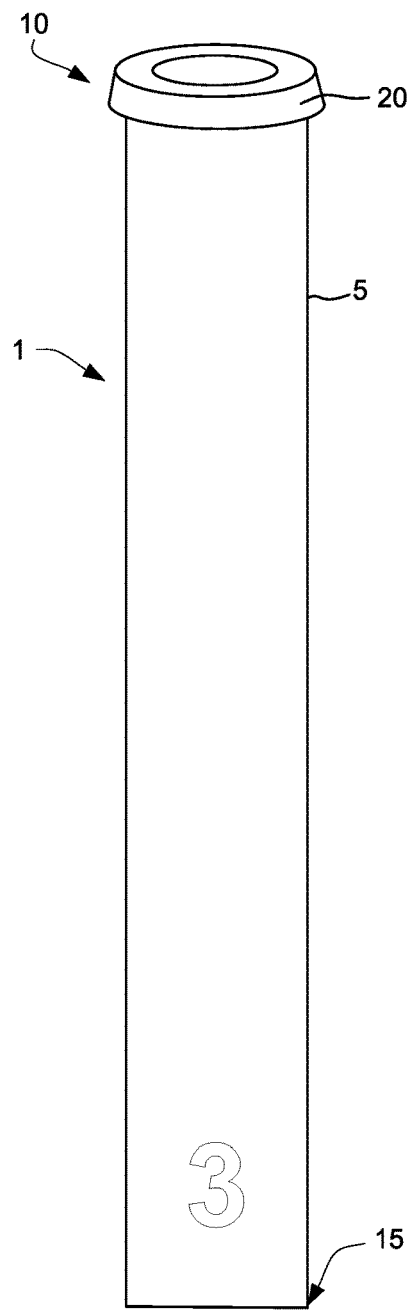
FIGS. 7A-7C illustrate views of a third size of a medical device according to an example of the present technology.
Figure 7B:
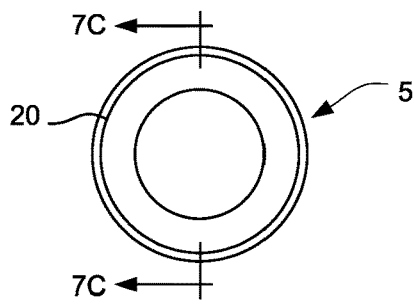
Figure 7C:
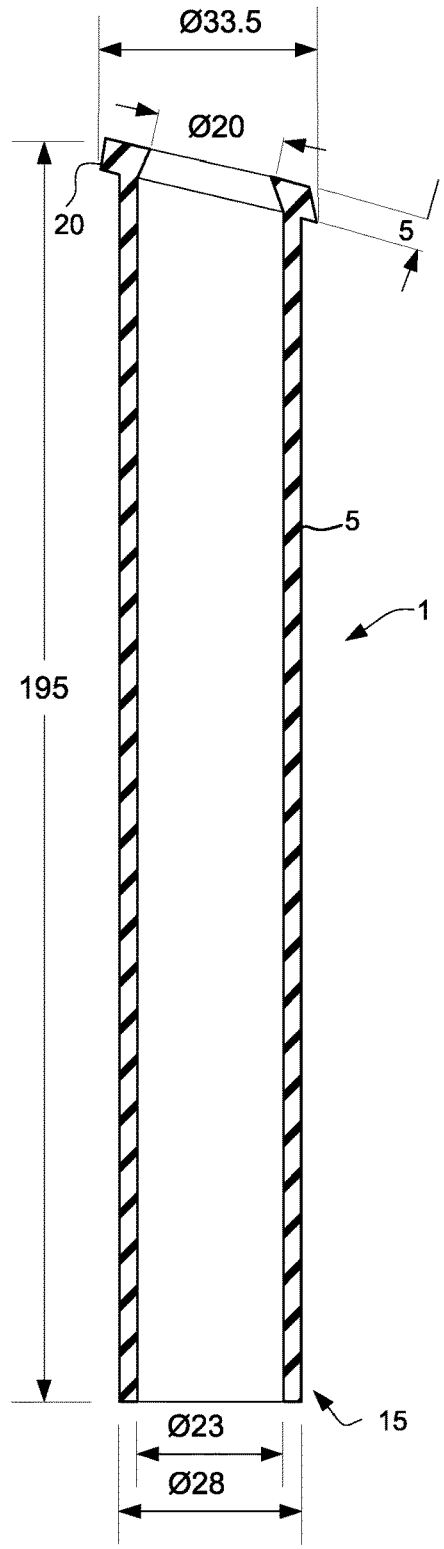
Figure 8A:
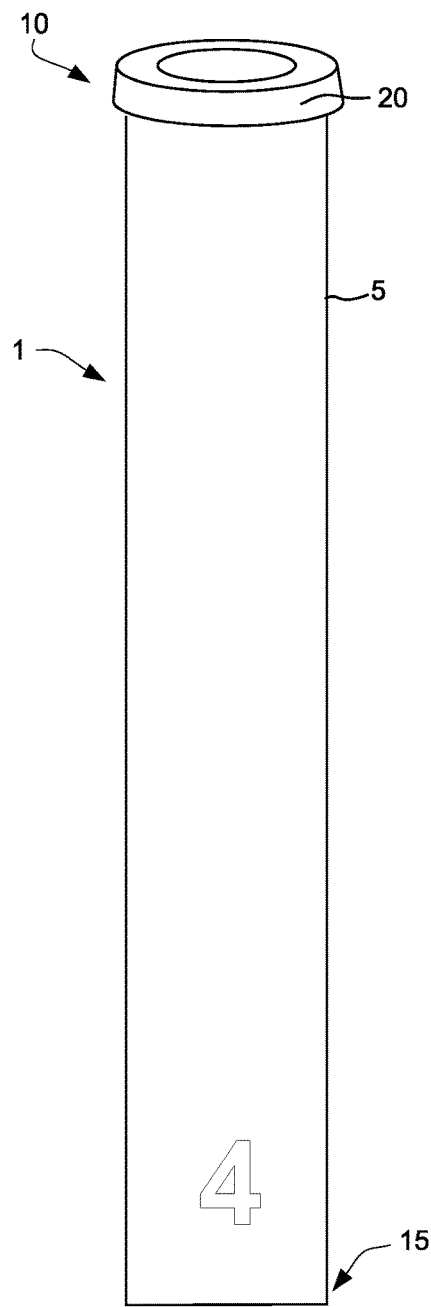
FIGS. 8A-8C illustrate views of a fourth size of a medical device according to an example of the present technology.
Figure 8B:
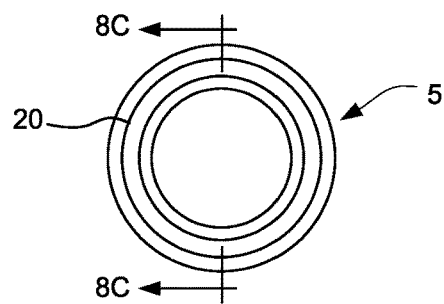
Figure 8C:
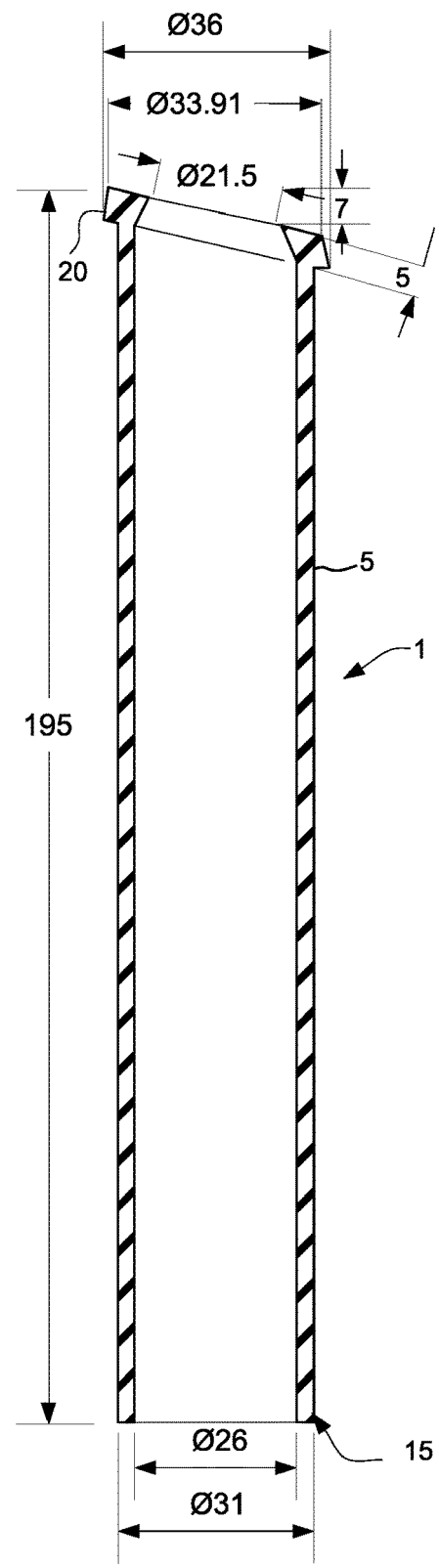
Figure 9A:
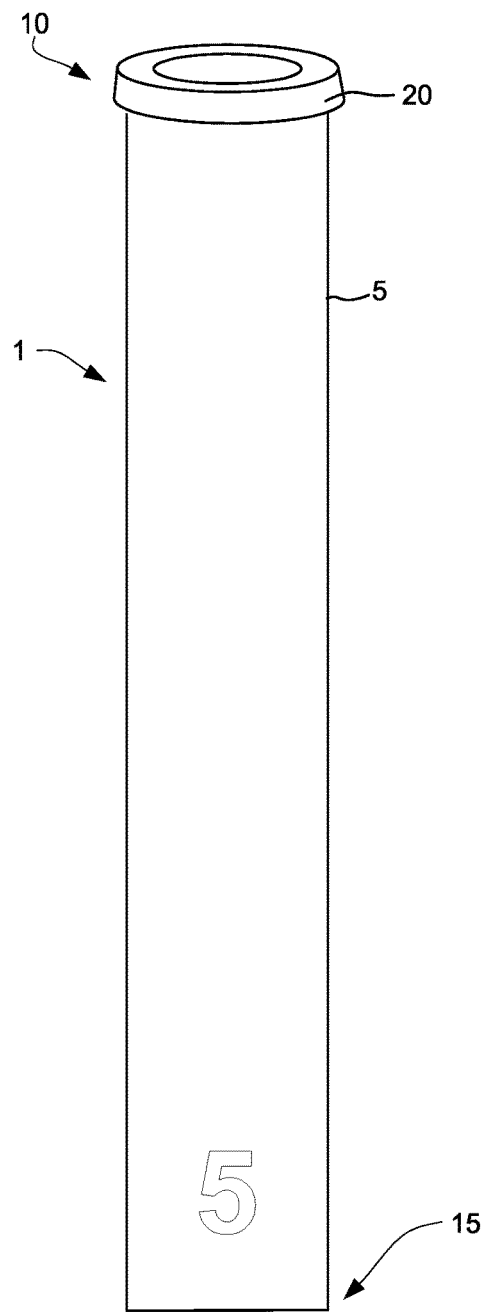
FIGS. 9A-9C illustrate views of a fifth size of a medical device according to an example of the present technology.
Figure 9B:
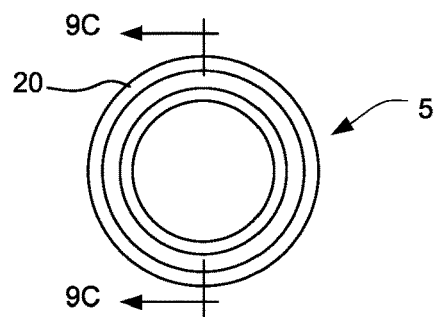
Figure 9C:
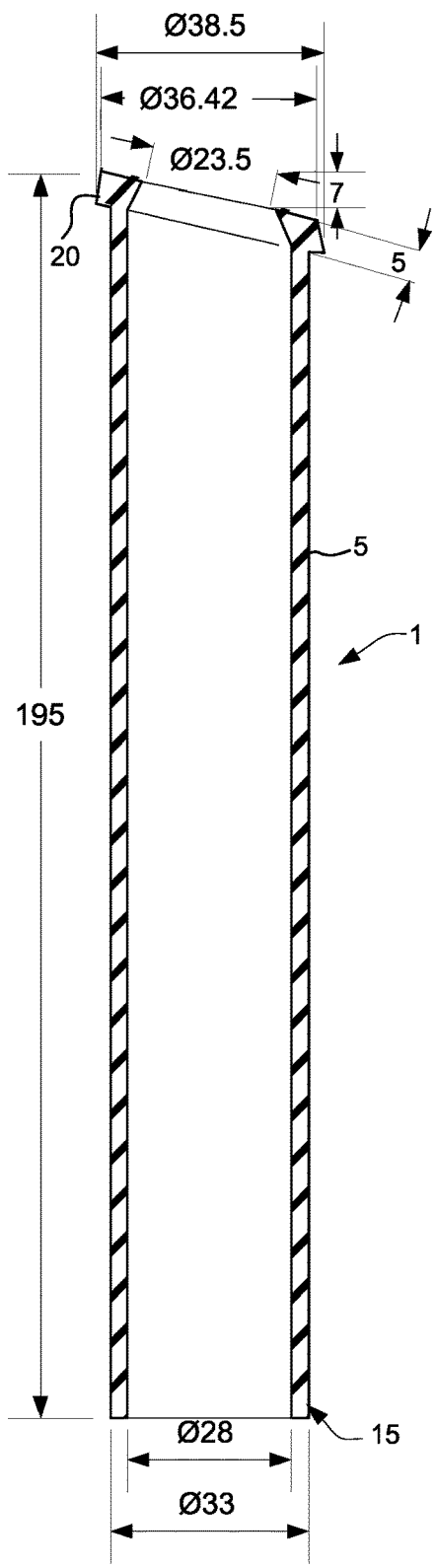
Figure 10A:
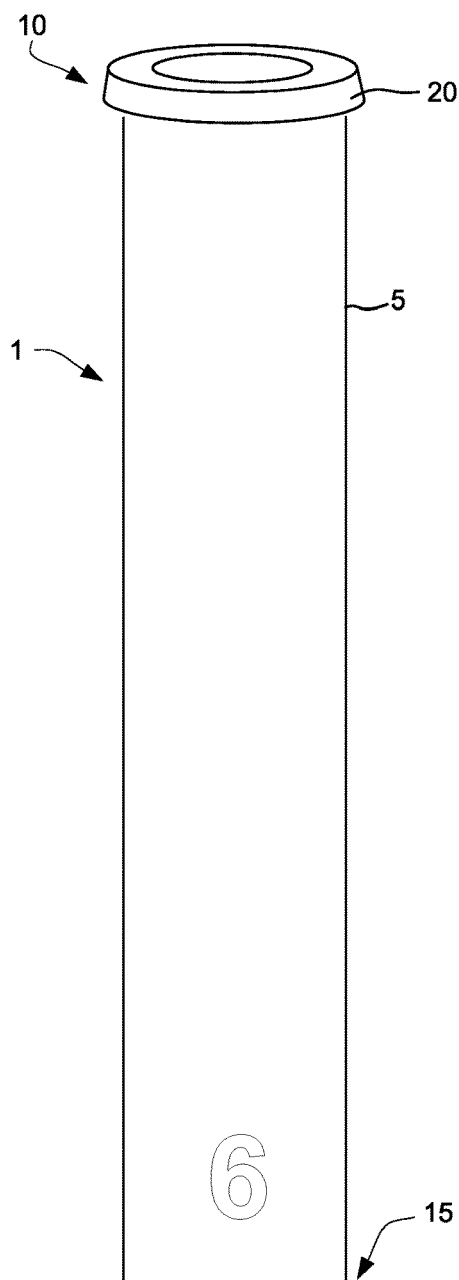
FIGS. 10A-10C illustrate views of a sixth size of a medical device according to an example of the present technology.
Figure 10B:
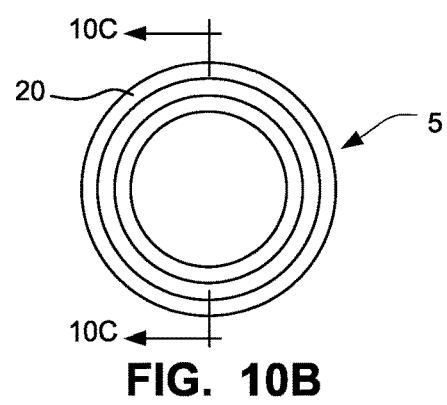
Figure 10C:
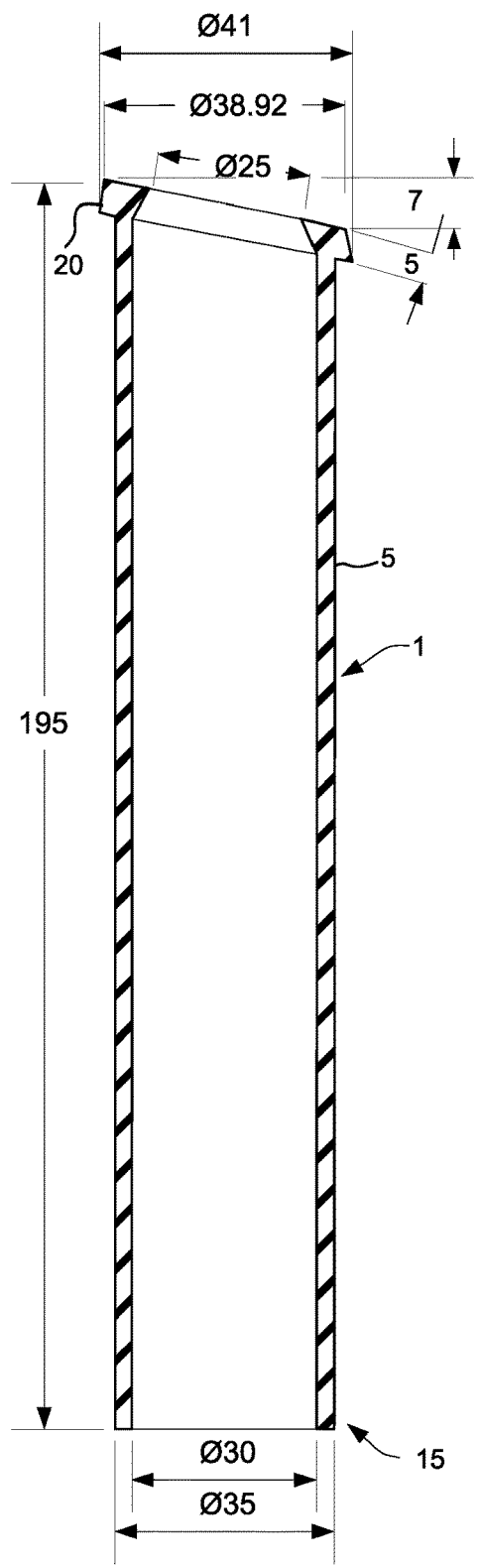
Figure 11A:
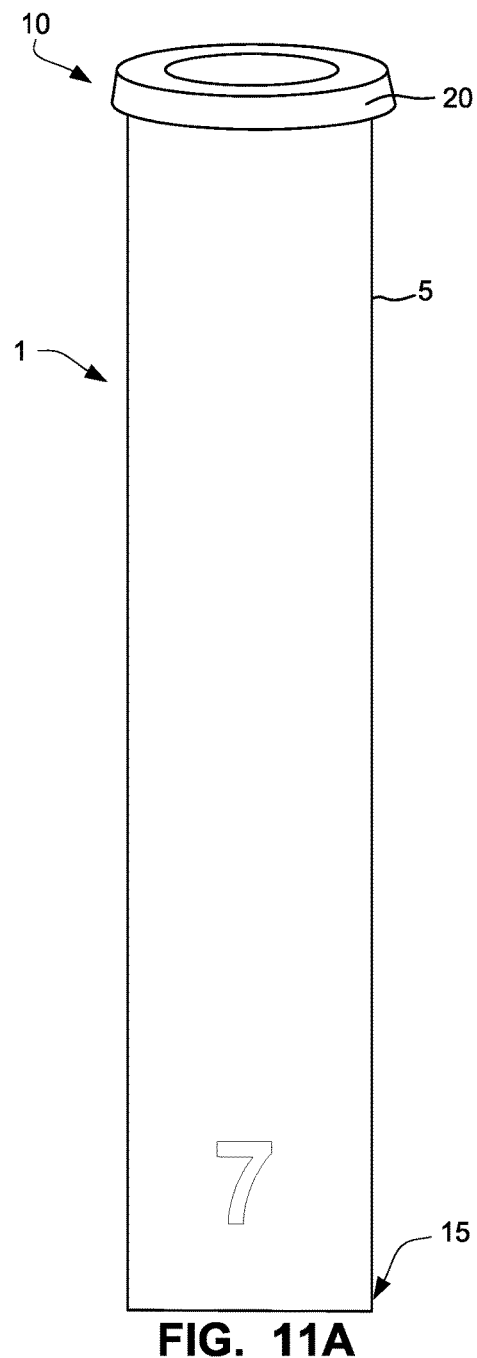
FIGS. 11A-11C illustrate views of a seventh size of a medical device according to an example of the present technology.
Figure 11B:
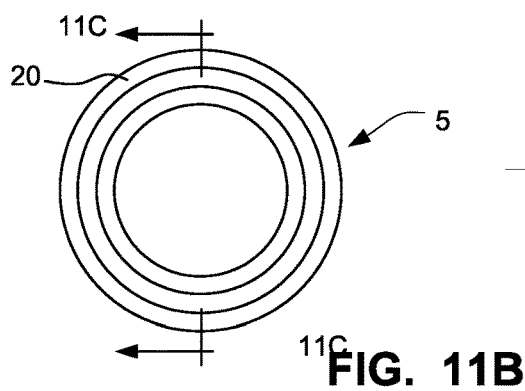
Figure 11C:
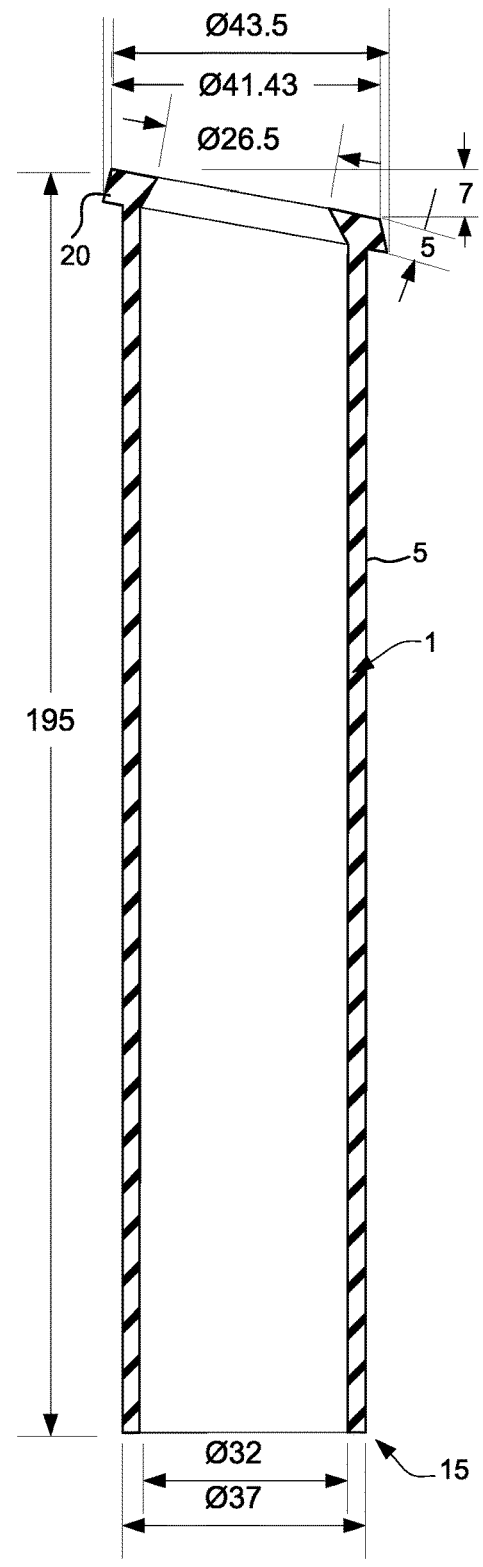
Figures 13A, 13B, 13C:
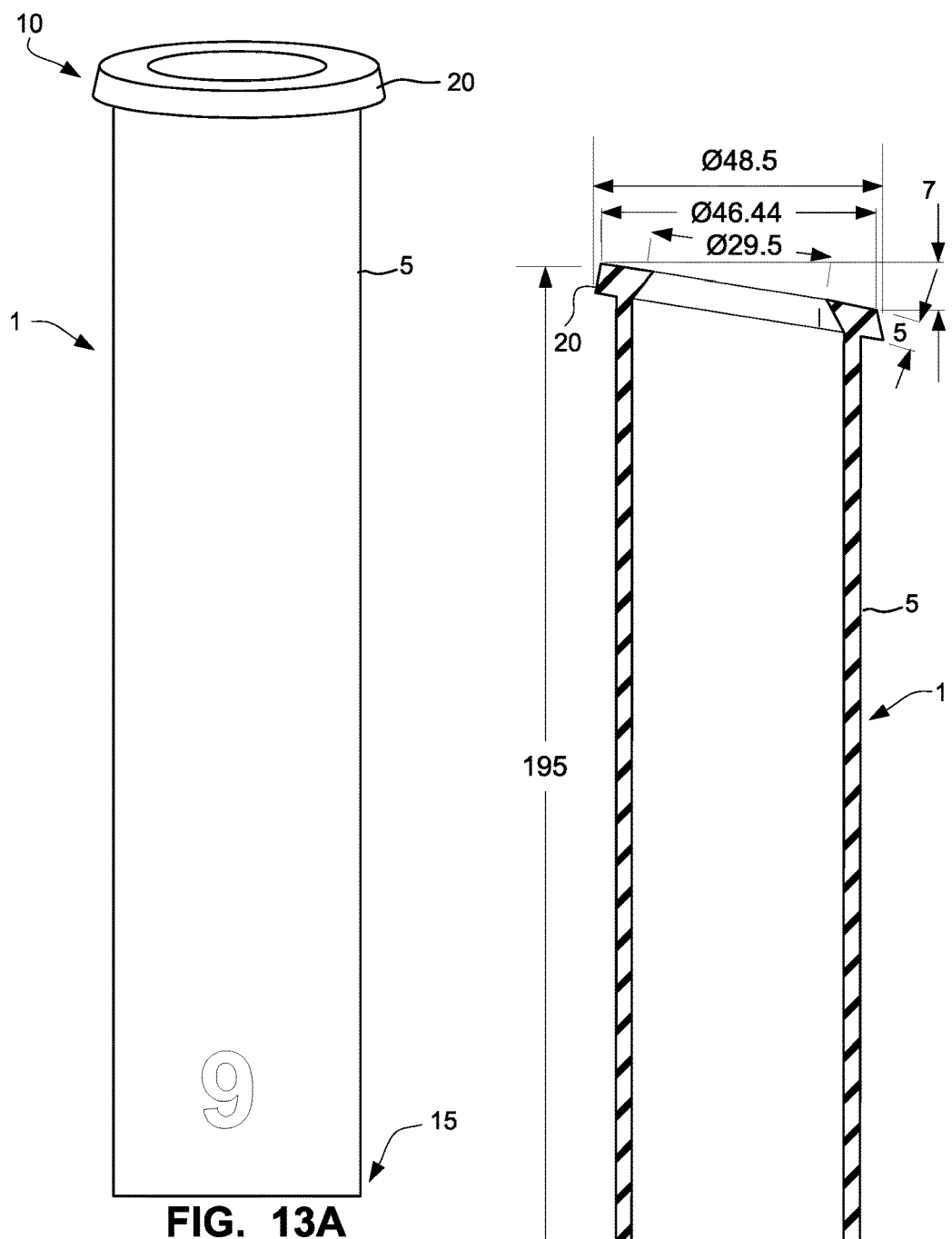
FIGS. 13A-13C illustrate views of a ninth size of a medical device according to an example of the present technology.

Due to variations in human anatomy, a physician may find it to be beneficial to have a plurality of different sizes of sleeves, in order to best fit the user or patient at hand. Thus, a kit for post procedural treatment for penile enhancement, including a plurality of flexible sleeves may be provided. The kit may include 2-15 different sized sleeves, e.g., 3 sizes or 10 sizes. As shown in FIGS. 5A-14C, showing 10 different sizes, each sleeve may be labeled with a size, e.g., "1", "2", "3", etc., to assist the physician in selecting the appropriately sized sleeve for a given patient or user. Each sleeve may a different inner diameter but substantially the same length and/or the same thickness. FIGS. 5A-14C show exemplary dimensions (in mm) which can vary up to 5-20 percent from what is shown. For convenience, FIGS. 5A to 14C have been labelled with reference numbers similar to those shown in FIGS. 1 to 3. FIGS. 5B, 8B, 9B, 10B, 11B, 12B, 13B and 14B show the bottom view of the sleeve, and FIGS. 6B and 7B show the top view of the sleeve.

WRAP—Variable Circumference

In addition, a sleeve 100 can be mounted on the penis in a way that is different than that shown in FIGS. 4A-4F. For example, the sleeve 100 can be separated along its longitudinal axis such that the sleeve has first 102 and second longitudinal edges 104. The sleeve may be wrapped around the penis, and secured. The sleeve may be formed of a textile material, as described above.

As shown in FIG. 15, the sleeve may start as a substantially flat sheet. However, the top of the sheet may have a curved shape, such that when wrapped about the penis, the top part is at an angle that is configured to match the shape of the corona of the glans, as described above. The sheet may have the thickness as described above in relation to the wall thickness TS of the sleeve. The sleeve may also have a length that is similar to the length L described in FIGS. 1-3. The sleeve may be cut to appropriate length before wrapping around the penis.

When wrapped, margins 106, 108 of the longitudinal edges 102, 104 at least partially overlap as shown in FIGS. 17-18. The overlapping margins 106, 108 can be releasably attached and connected in a number of different manners, e.g., zipper, hook and loop fastener (e.g., VELCRO®), adhesive (e.g., biocompatible adhesive), one or more snaps, etc. Moreover, the material of the sleeve may have an adhesive property. The edges may also be permanently attached or affixed. FIG. 18 shows that one margin, e.g. 108, covers the other margin 106 (shown in hidden lines). The margin 108 forms a seam 110 that is located on the outer surface of the sleeve.

FIG. 17 schematically shows that the margins 106, 108 include a hook and loop fastener (hooks and loops) or adhesive, indicated as xxx. FIG. 19 shows that the margins may include a snap arrangement 110 including at least one protruding snap 112 and one or more snap recesses 114. FIG. 20 shows a hook and eye arrangement 116 (such as the type used for a women's brassiere), including at least one hook 118 and at least one hook recess 120 or loop. As shown in FIG. 20, the margin with the recess 120 or loop may also include a flap 121 that helps protect the user's skin from the hook 118. The flap 121 may be integrally formed in one piece with the margin, or it may be that the flap is made of a different material (e.g., textile), while the margin with the recesses can be made of another material, e.g., silicone. FIG. 21 shows an arrangement where one of the margins 106, 108 includes a protrusion 122 and the other margin includes a plurality of recesses 124. FIG. 21 also shows that one of the edges includes a flap 126 that surrounds an outer surface of the marginal edge, creating a sandwich type structure. The flap may be affixed to the edge via adhesive and/or hook and loop. In some forms, a plurality of such fasteners (e.g., 2, 3, 4, 5, 6 or more) could be provided along the seam or longitudinal axis to attach the edges or margins to one another.

As is apparent from the above description, the circumference or diameter of the sleeve can be adjusted to a size that is appropriate for the wearer's penis, e.g., by stretching in the circumferential direction and connecting the margins once the sleeve reaches the appropriate circumference. The circumference of the sleeve will preferably be slightly less than the circumference of the penis, to allow for appropriate compression. This might be helpful so that it is not necessary to provide as many different sizes, compared to FIGS. 5A-14C. However, different sizes of the sleeve shown in FIG. 15 can also be provided, similar to FIGS. 5A-14C. FIG. 15 shows the exterior surface of the sleeve.

The sleeve may include a flange 130 as described above, but it need not have a flange. The flange is shown in FIGS. 15-18. The flange may be dimensioned such that it has a width w that is less than the width W of the sleeve, as shown in FIGS. 15, 17 and 18. This is helpful as it allows some variation in the distance the margins overlap, and the circumferential ends of the flange will not interfere with one another. However, the ends of the flange could also be connected as shown in FIGS. 19-21. In an example, the flange can be made of medical grade silicone and molded (e.g., insert molded) onto the sleeve, which can be made of a textile. Alternatively, the flange could be in the form of a silicone bead that is applied to the top edge of the textile material.

Different features, variations and multiple different examples have been shown and described with various details. What has been described in this application at times in terms of specific examples is done for illustrative purposes only and without the intent to limit or suggest that what has been conceived is only one particular example or specific examples. It is to be understood that this disclosure is not limited to any single specific example or enumerated variations. Many modifications, variations and other examples will come to mind of those skilled in the art, and which are intended to be and are in fact covered by both this disclosure.

While the present technology has been described in connection with what is presently considered to be some practical and preferred examples, it is to be understood that the present technology is not to be limited to the disclosed examples, but on the contrary, is intended to cover various modifications and equivalent arrangements included within the spirit and scope of the disclosure.

The invention claimed is:

1. A medical device for placing on a human penis, the medical device comprising:
   a flexible sleeve having a proximal end and a distal end, the proximal end being sized and dimensioned to be positioned over the base of the penis, the sleeve being configured and sized to extend from the base of the penis and along the body of the penis, the distal end being sized and dimensioned to terminate just below the corona of the glans of the penis, wherein the sleeve from the distal end to the proximal end has a closed loop shape in cross section, and has a solid wall portion with substantially no openings or interruptions,
   wherein the sleeve has a longitudinal axis and is rollable along the longitudinal axis,
   wherein the flexible sleeve is configured to compress the penis from the base to just below the glans, and
   wherein the distal end has a terminal end with a terminal end inner diameter that is less than an inner diameter of the remainder of the flexible sleeve, the terminal end inner diameter of the distal end being configured to help prevent the head of the penis from retracting into the flexible sleeve,
   wherein the distal end includes a flange that extends radially outwards from an outer surface of the sleeve, the flange having a top edge with a shape configured to match the shape of the corona of the glans of the penis.

2. The medical device of claim 1, wherein the distal end includes a flange that extends radially outwards from an outer surface of the sleeve, wherein the flange is about 5 mm in thickness, and wherein a thickness of the sleeve spaced away from the flange along a longitudinal axis of the sleeve is about 2 mm-3 mm.

3. The medical device of claim 1, wherein a thickness of the sleeve is about 0.5-5 mm from the distal end to the proximal end.

4. The medical device of claim 3, wherein a wall thickness of the sleeve is about 2-3 mm or 2.5 mm.

5. The medical device of claim 1, wherein the inner diameter of the sleeve is about 15-50 mm.

6. The medical device of claim 5, wherein the inner diameter is about 20-40 mm.

7. The medical device of claim 1, wherein a length of the sleeve is about 180-220 mm.

8. The medical device of claim 1, wherein the sleeve is configured to be moved from an unrolled position to a rolled position by rolling the proximal end radially outwards and axially towards the distal end, wherein the terminal end inner diameter is positioned at the terminal end in both the rolled position and the unrolled position.

9. The medical device of claim 8, wherein, in the rolled position, the sleeve is stretchable from a first diameter to a second diameter.

10. The medical device of claim 1, wherein the sleeve includes an indicator or indicia to indicate what side is intended to be the superior side when in place on the penis.

11. The medical device of claim 1, wherein an inner diameter of the flange is less than an inner diameter of the distal end of the sleeve.

12. The medical device of claim 1, wherein the flange is contained in a plane that is angled relative to a longitudinal axis of the sleeve.

13. The medical device of claim 12, wherein the plane is angled about 1-15 degrees relative to the longitudinal axis of the sleeve.

14. The medical device of claim 1, wherein a diameter of the flange is about 2-10 mm greater than an outer diameter of the sleeve spaced axially away from the flange.

15. The medical device of claim 1, wherein a thickness of the flange is about 2-8 mm.

16. The medical device of claim 15, wherein the thickness of the flange is about 5 mm.

17. The medical device of claim 1, wherein an inner diameter of the flange includes an inwardly angled portion in the form of a cone that forms an angle relative to an inner surface of the sleeve adjacent the flange, the inner surface of the sleeve having a cylindrical shape and the inwardly angled portion extending from the cylindrical shape and tapering down from the cylindrical shape to the terminal end of the distal end of the sleeve.

18. The medical device of claim 1, wherein the sleeve is made of medical grade silicone, wherein the silicone has a Shore A hardness of 2 to 5, +/−20%.

19. The medical device of claim 1, wherein the sleeve is configured to compress and/or elongate the penis.

20. The medical device of claim 1, wherein the sleeve is configured to resist migration of at least one girth enhancement product injected into the penis.

21. A kit for post procedural treatment for penile enhancement, including a plurality of flexible sleeves according to claim 1, wherein each said sleeve has a different inner diameter but substantially the same length and/or substantially the same thickness.

22. The medical device of claim 1, wherein the sleeve includes only a single layer configured and sized to extend from the base of the penis, along the body of the penis, and terminate just below the corona of the glans of the penis.

23. A device for placing on a human penis, the device consisting of:
    a flexible sleeve consisting of a single layer of homogeneous material, the sleeve having a proximal end and a distal end, the proximal end being sized and dimensioned to be positioned over the base of the penis, the sleeve being configured and sized to extend from the base of the penis and along the body of the penis, the distal end being sized and dimensioned to terminate just below the corona of the glans of the penis,
    wherein the sleeve is configured to compress the penis from the base or proximal shaft of the penis to just below the corona of the glans or head of the penis, and is configured to expand in place as the penis becomes erect, and yet is sufficiently firm or rigid to hold the penis extended,
    wherein the distal end includes a flange that extends radially outwards from an outer surface of the sleeve, wherein the flange is about 5 mm in thickness, and wherein a wall thickness of the sleeve spaced away from the flange along a longitudinal axis of the sleeve is about 2 mm-3 mm,
    wherein an inner diameter of the flange includes an inwardly angled portion in the form of a cone that forms an angle relative to an inner surface of the sleeve adjacent the flange,
    wherein the flange is contained in a plane and the plane is angled about 1-15 degrees relative to the longitudinal axis of the sleeve, and
    wherein the flexible sleeve is made of medical grade silicone having a wall thickness of 2 mm-3 mm.

24. A medical device for placing on a human penis, the medical device comprising:
    a flexible sleeve having a proximal end and a distal end, the proximal end being sized and dimensioned to be positioned over the base of the penis, the sleeve being configured and sized to extend from the base of the penis and along the body of the penis, the distal end being sized and dimensioned to terminate just below the corona of the glans of the penis, wherein the sleeve from the distal end to the proximal end has a closed loop shape in cross section, and has a solid wall portion with substantially no openings or interruptions,
    wherein the sleeve has a longitudinal axis and is rollable along the longitudinal axis,
    wherein the flexible sleeve is configured to compress the penis from the base to just below the glans, and
    wherein the distal end has a terminal end with a terminal end inner diameter that is less than an inner diameter of the remainder of the flexible sleeve, the terminal end inner diameter of the distal end being configured to help prevent the head of the penis from retracting into the flexible sleeve; and
    wherein the distal end includes a flange that extends radially outwards from an outer surface of the sleeve, wherein the flange is about 5 mm in thickness, and wherein a thickness of the sleeve spaced away from the flange along a longitudinal axis of the sleeve is about 2 mm-3 mm.

\* \* \* \* \*